United States Patent
Hamilton et al.

(10) Patent No.: US 6,881,939 B1
(45) Date of Patent: Apr. 19, 2005

(54) MICROPROCESSOR BASED AUTOMATICALLY DIMMABLE EYE PROTECTION DEVICE

(75) Inventors: Thomas J. Hamilton, Holland, MI (US); Barry D. Scott, Orleans, MI (US)

(73) Assignee: Jackson Products, Inc., St. Charles, MO (US)

( * ) Notice: Subject to any disclaimer, the term of this patent is extended or adjusted under 35 U.S.C. 154(b) by 258 days.

(21) Appl. No.: 10/140,049

(22) Filed: May 3, 2002

Related U.S. Application Data

(60) Provisional application No. 60/288,759, filed on May 5, 2001.

(51) Int. Cl.[7] .............................. H01J 40/14; G01J 1/32
(52) U.S. Cl. ................ 250/205; 250/214 R; 250/201.1; 349/14
(58) Field of Search ............................. 250/205, 214 R, 250/214 RC, 214 B, 201.1; 349/13, 14, 116; 2/8

(56) References Cited

U.S. PATENT DOCUMENTS

| | | |
|---|---|---|
| 2,423,320 A | 7/1947 | Hurley |
| 2,548,230 A | 4/1951 | Molyneux |
| 2,761,048 A | 8/1956 | Herrick et al. |
| 3,137,784 A | 6/1964 | Kasemann |
| 3,159,844 A | 12/1964 | Haboush |
| 3,245,315 A | 4/1966 | Marks et al. |
| 3,575,491 A | 4/1971 | Hellmeier |
| 3,731,986 A | 5/1973 | Fergason |
| 3,873,804 A | 3/1975 | Gordon |
| 3,881,808 A | 5/1975 | Gurtler et al. |
| 3,881,809 A | 5/1975 | Fergason et al. |
| 3,890,628 A | 6/1975 | Gurtler |
| 3,918,796 A | 11/1975 | Fergason |
| 3,967,881 A | 7/1976 | Moriyama et al. |
| 4,039,803 A | 8/1977 | Harsch |
| 4,071,912 A | 2/1978 | Budmiger |
| RE29,684 E | 6/1978 | Gordon |

(Continued)

FOREIGN PATENT DOCUMENTS

| | | |
|---|---|---|
| CH | 73127334 | 7/1977 |
| CH | 7608690-9 | 2/1979 |
| DE | 2315308 | 10/1973 |
| EP | 0335056 | 4/1989 |
| EP | 0349665 | 10/1990 |
| EP | 0157744 | 9/1995 |
| FR | 2530-039 A | 1/1984 |
| GB | 325586 | 2/1930 |
| JP | 59-92276 | 7/1980 |
| JP | 59-111102 | 6/1984 |
| WO | WO 90/14809 | 12/1990 |

*Primary Examiner*—Kevin Pyo
(74) *Attorney, Agent, or Firm*—Dunlap, Codding & Rogers, P.C.

(57) ABSTRACT

An auto darkening eye protection device comprising a shutter assembly adjustable between a clear state and a dark state and a control circuit. The control circuit is provided with a microcontroller, a delivery circuit, a sensing circuit and a weld detect circuit. The microcontroller is switchable between a sleep mode and a wake-up mode. The delivery circuit outputs a dark state drive signal to the shutter assembly to switch the shutter assembly from the clear state to the dark state upon enablement of the delivery circuit. The sensing circuit senses the occurrence of a welding arc and provides an output indicative of the occurrence of the welding arc. The weld detect circuit receives the output of the sensing circuit. The weld detect circuit enables a dark state drive signal to be delivered to the shutter assembly by the delivery circuit, and a signal to be delivered to the microcontroller to switch the microcontroller from the sleep mode to the wake-up mode whereby the shutter assembly is switched to the dark state without the aid of the microcontroller.

7 Claims, 16 Drawing Sheets

U.S. PATENT DOCUMENTS

| | | | |
|---|---|---|---|
| 4,155,122 A | 5/1979 | Budmiger |
| 4,237,557 A | 12/1980 | Gordon |
| 4,240,709 A | 12/1980 | Hornell |
| 4,279,474 A | 7/1981 | Belgorod |
| 4,328,490 A | 5/1982 | Usuba et al. |
| 4,385,806 A | 5/1983 | Fergason |
| 4,435,047 A | 3/1984 | Fergason |
| 4,436,376 A | 3/1984 | Fergason |
| 4,540,243 A | 9/1985 | Fergason |
| 4,556,289 A | 12/1985 | Fergason |
| 4,560,239 A | 12/1985 | Katz |
| 4,582,396 A | 4/1986 | Bos et al. |
| 4,664,479 A | 5/1987 | Hiroshi |
| RE32,521 E | 10/1987 | Fergason |
| 4,710,694 A | 12/1987 | Sutphin et al. |
| 4,728,173 A | 3/1988 | Toth |
| 4,759,608 A | 7/1988 | Yang |
| 4,813,766 A | 3/1989 | Keene et al. |
| 4,821,292 A | 4/1989 | Childress |
| 4,863,244 A | 9/1989 | Fuerthbauer et al. |
| 4,877,310 A | 10/1989 | Seachman et al. |
| 4,901,074 A | 2/1990 | Sinn et al. |
| 4,928,181 A | 5/1990 | Harward |
| 5,015,086 A | 5/1991 | Okaue et al. |
| 5,074,647 A | 12/1991 | Fergason et al. |
| 5,113,270 A | 5/1992 | Fergason |
| 5,184,156 A | 2/1993 | Black et al. |
| 5,208,688 A | 5/1993 | Fergason et al. |
| 5,248,880 A | 9/1993 | Fergason |
| 5,252,817 A | 10/1993 | Fergason et al. |
| 5,347,383 A | 9/1994 | Fergason |
| 5,377,032 A | 12/1994 | Fergason et al. |
| 5,420,502 A | 5/1995 | Schweitzer, Jr. |
| 5,519,522 A | 5/1996 | Fergason |
| 5,671,035 A | 9/1997 | Barnes |
| 5,751,258 A * | 5/1998 | Fergason et al. ............... 345/7 |
| 6,067,129 A | 5/2000 | Fergason |
| 6,070,264 A | 6/2000 | Hamilton et al. |
| 6,552,316 B1 * | 4/2003 | Bae ..................... 250/201.1 |

* cited by examiner

US 6,881,939 B1

MICROPROCESSOR BASED AUTOMATICALLY DIMMABLE EYE PROTECTION DEVICE

CROSS REFERENCE TO RELATED APPLICATIONS

The present patent application claims priority to the provisional patent application identified by U.S. Ser. No. 60/288,759 and filed on May 5, 2001, the entire content of which is hereby expressly incorporated herein by reference.

DETAILED DESCRIPTION OF THE INVENTION

Figure 1:
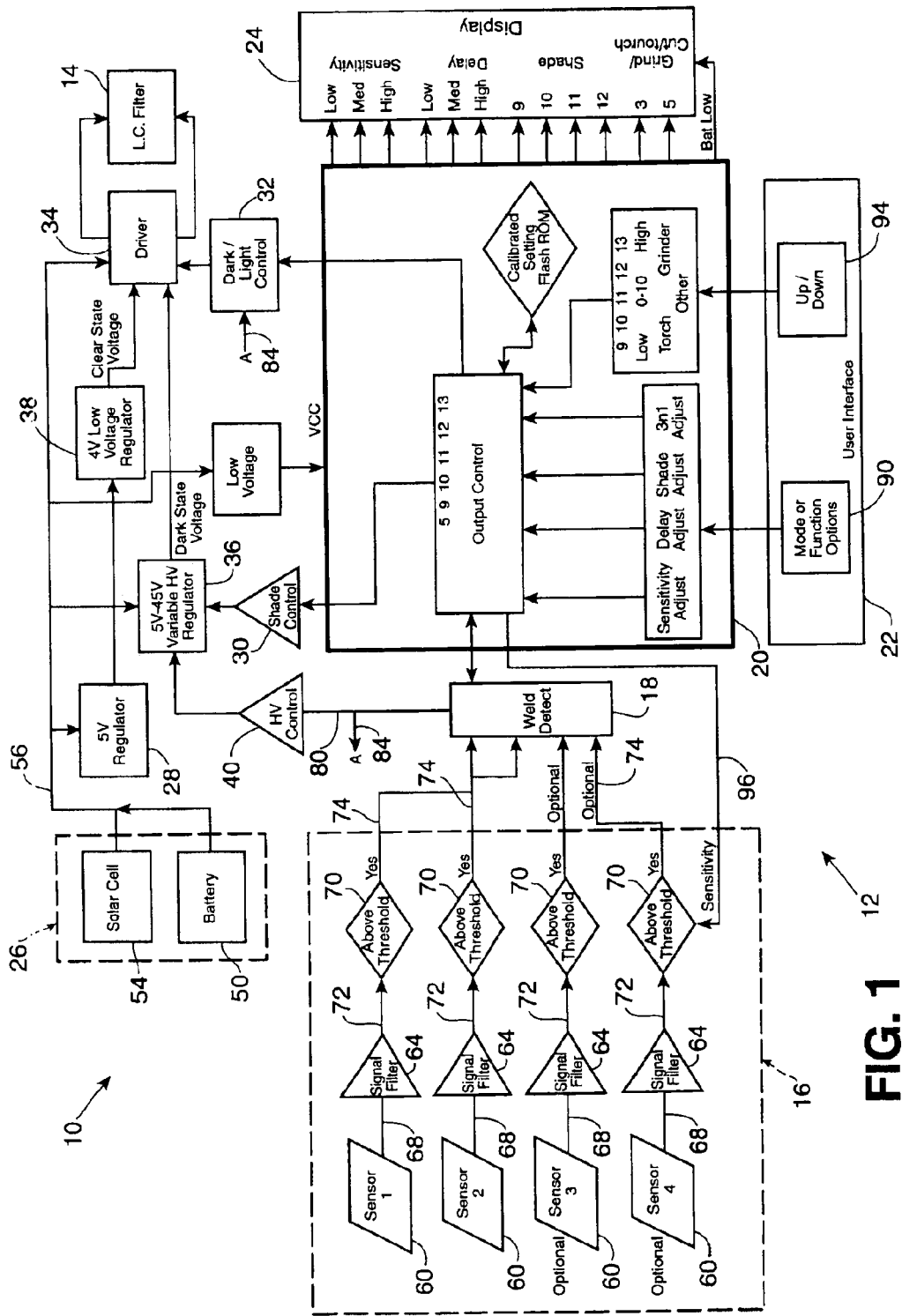
FIG. 1 is a block diagram of an eye protection device constructed in accordance with the present invention.

The eye protection device 10 is provided with a control circuit 12, and a shutter assembly 14. The shutter assembly 14 is an auto-darkening filter capable of being driven between a "clear state" and a "dark state". In the clear state, an individual can see through the shutter assembly 14 under ambient light conditions. In the dark state, the shutter assembly 14 typically becomes opaque so that the individual can only see through the shutter assembly 14 in the presence of an intense light, such as a welding arc. As will be discussed in more detail below, the opacity of the shutter assembly 14 can be varied.

The switching speed of the eye protection device 10 is an important performance attribute of the eye protection device 10. As will be well understood by those skilled in the art, the switching speed is the time period for switching the shutter assembly 14 from the clear state to the dark state. As will be discussed in more detail below, in accordance with the present invention, a "dark state" drive signal having a high voltage pulse, e.g. 30–45 V, is provided to the shutter assembly 14 to enhance the switching speed of the shutter assembly 14. The shutter assembly 14 is preferably a liquid crystal display, such as a twisted nematic liquid crystal display or a pi-cell liquid crystal display.

The control circuit 12 senses the intense light and outputs the "dark state" drive signal to the shutter assembly 14 to cause the shutter assembly 14 to switch from the clear state to the dark state. If the control circuit 12 senses that no welding arc is present, the control circuit 12 will cause a "clear state" drive signal to be delivered to the shutter assembly 14.

The control circuit 12 includes a sensor circuit 16, a weld detect circuit 18, a microcontroller 20, a user interface 22, a display 24, a power supply 26, a voltage regulator 28, a shade control 30, a dark/light control 32, a driver 34, a variable high voltage regulator 36, a low voltage regulator 38, and a high voltage control 40. As will be discussed in more detail below, in accordance with the present invention, the control circuit 12 provides a variety of useful features not available in analog control circuits. That is, the microcontroller 20 can learn, and store information so as to provide features such as automatic light sensitivity, automatic shade control, memory presets, and selectable torch shade settings.

The microcontroller 20 can be implemented as a microcontroller, a microprocessor having internal or external circuitry to function as a microcontroller, or a microcontroller/ASIC having internal or external circuitry to a function as a microcontroller.

The power supply 26 includes a battery power supply 50, and a solar power supply 54. The battery power supply 50 and the solar power supply 54 provide electrical power to the voltage regulator 28 via a power line 56.

The battery power supply 50 can be provided with any suitable voltage so as to supply power to the control circuit 12 and the shutter assembly 14. For example, the battery power supply 50 can be provided with a voltage in a range from about 2.0 V to about 6.5 V. In a preferred embodiment depicted in FIG. 2, the battery power supply 50 has about 6 Volts.

The voltage regulator 28 receives the power generated by the battery power supply 50 and the solar power supply 54. In response thereto, the voltage regulator 28 regulates the power to provide a stable voltage of preferably about 5 Volts. The voltage regulator 28 provides electrical power to all of the components in the control circuit 12.

The sensor circuit 16 includes a plurality of sensors 60 for detecting the presence of light and outputting a sensor output signal representative of the level of light detected. The sensors 60 are preferably phototransistors. However, photodiodes or other types of light sensors could be used.

The sensor output signals are output to a plurality of signal filters 64 via signal paths 68. The signal filters 64 are in series with the comparators 70. The signal filters 64 are preferably high pass filters tuned at about 100–120 Hz so as to block ambient light signals formed by 50/60 Hz lighting. In accordance with the present invention, each of the signal filters 64 preferably include a resistor, positioned in parallel with the high pass filter so as to permit the signal filters 64 to pass at least some DC bias generated by the sensors 60. Each of the high pass filters can be formed by a capacitor resistor circuit. The high pass filters allow AC signals to pass to a detection circuit, e.g., the comparator 70, and thus the weld detect circuit 18 during AC welding. The high pass filters also provides the signal in the initial start of the weld because of the quick change in the light. The high pass filters rely on the signal caused by variations in the light while welding. During DC welding, the light is very smooth and little AC components are generated. Therefore, the resistor is added to allow DC biasing to affect the sensitivity. The brighter the light into the sensors 60, the higher the DC component. Some of this bias is then passed to the detection circuit, e.g. the comparator 70, via the resistor to increase the sensitivity and aid in the detection of the smooth weld.

The outputs of the signal filters 64 are fed to a plurality of comparators 70 via signal paths 72 to determine if the outputs of the signal filters 64 are above a predetermined threshold. The predetermined threshold will depend on the biasing level of the comparators 70 during ambient light conditions. For example, the sensitivity threshold can be in a range from about +0.5 V to about +1.75 V. The DC ambient bias level (from the resistor) can be in a range from about 0 V to about 0.5 V above the AC ambient bias level, e.g. +0.0 V to about +1.25 V of the comparators 70. For instance, once the ambient biasing level exceeds the sensitivity threshold, the comparator 70 will output a signal causing the shutter assembly 14 to go dark. The outputs of the comparators 70 are ORed together. Thus, when the outputs of any one of the signal filters 64 are above the predetermined threshold, a signal is transmitted to the weld detect circuit 18 via signal paths 74 to cause a dark state drive signal to be delivered to the shutter assembly 14. When the outputs are below the predetermined threshold, the weld detect circuit 18 will cause a "clear state" drive signal to be delivered to the shutter assembly 14.

One preferred embodiment of the weld detect circuit 18 is shown in the schematic diagram of FIG. 2. The weld detect circuit 18 includes an electronic switch circuit, such as a transistor circuit, receiving the signal from the sensor circuit 16. The electronic switch circuit includes an electronic switch, such as a transistor. In accordance with the present invention, a capacitor C6 is connected in parallel with the electronic switch to increase the switching speed of the electronic switch circuit. For example, the electronic switch can be a transistor, and the capacitor can be connected between the collector of the transistor and ground. The electronic switch can be any suitable switching component, such as a transistor, a JFET, a MOSFET, or the like.

When the electronic switch circuit receives the signal indicative of the welding arc from the sensor circuit 16, a capacitor C5 provides an initial high current spike to quickly change the state of the electronic switch. This initial high current spike increases the switching speed of the electronic switch so as to increase the switching speed of the eye protection device 10.

The dark state drive signal is continuously generated by the variable high voltage regulator 36. The clear state drive signal is continuously generated by the low voltage regulator 38. When the shutter assembly 14 is a twisted nematic type LCD display, the low voltage regulator 38 can be omitted. The driver 34 simultaneously receives the dark state drive signal and the clear state drive signal and selectively passes the dark state drive signal or the clear state drive signal to the shutter assembly 14 so as to regulate the opacity of the shutter assembly 14. The dark/light control 32 transmits signals to the driver 34 which controls passage of the clear state drive signal or the dark state drive signal through the driver 34.

In one preferred embodiment, the driver 34 periodically switches the polarity of the clear state drive signal and the dark state drive signal so that the clear state and dark state drive signals transmitted to the shutter assembly 14 oscillate at any desired frequency. Typically, the frequency of oscillation will be between about 35 and 60 Hz. That is, if the oscillation of the clear state and dark state drive signals is below about 35 Hz, then the shutter assembly 14 may appear to flicker, which can be annoying for the user. If the oscillation of the clear state and dark state drive signals is above about 60 Hz, then the shutter assembly 14 will draw more power. If the shutter assembly 14 is a twisted nematic type of liquid crystal device, a desirable frequency of oscillation is about 35 to about 42 Hz. To further conserve power, the frequency of oscillation for the twisted nematic type of liquid crystal device can be as low as about 0.1 Hz. If the shutter assembly 14 is a Pi-cell type of liquid crystal device, a desirable frequency of oscillation is about 40 Hz to about 55 Hz.

The dark state drive signal is provided with two components; a HV pulse immediately followed by a constant voltage. The HV pulse is provided with a relatively high voltage in a range from about 30 V to about 120 V so as to quickly drive the shutter assembly 14 from the clear state to the dark state. The constant voltage has a reduced voltage preferably in a range from about 5 V to about 20 V to maintain the shutter assembly 14 in the dark state. The HV pulse preferably has a voltage in a range from about 15 V to about 120 V and a time period from about 10 microseconds to about 100 milliseconds. In general, the voltage of the HV pulse will depend on the maximum voltage ratings of the components utilized to implement the control circuit 12. In one preferred embodiment, the voltage of the HV pulse is about 30–45 V, and the time period of the HV pulse is about 1–3 ms. When the shutter assembly 14 is a pi-cell liquid crystal display, the constant voltage can be in the range from about 5 V to about 20 V.

To increase the switching speed of the shutter assembly 14, the variable high voltage regulator 36 continuously generates a first signal and a second signal having different voltages. The first signal is passed to the driver 34 for a selected time period to form the HV pulse, at the end of which the second signal is passed to the driver 34 to form the constant voltage.

In general, the HV control 40 communicates with the variable high voltage regulator 36 so as to control the switching of the first and second signals to form the HV pulse followed by the constant voltage. The HV control 40 can be formed by an RC circuit with the time constant of the RC circuit determining the time period of the HV pulse. The microcontroller 20 communicates with the HV control 40 when the eye protection device 10 is turned on so as to initialize the shutter assembly 14. During initialization, the shutter assembly 14 is enabled to the dark state for a predetermined time period. In the preferred embodiment depicted in FIG. 2, the microcontroller 20 only communicates with the HV control 40 to initialize the shutter assembly 14.

The shade control 30 adjusts the voltage level of the second signal so as to adjust the opacity of the shutter assembly 14 in the dark state. For example, the shade control 30 can be formed by a digital potentiometer positioned in a voltage divider circuit.

In use, when the eye protection device 10 is in a weld mode and the sensor output signal indicates to the weld detect circuit 18 that an intense light, such as a welding arc is present, the weld detect circuit 18 outputs a signal to the HV control 40 and the dark/light control 32 via signal paths 80 and 84 to simultaneously cause the variable high voltage regulator 36 to output the dark state drive signal, and the dark/light control 32 to switch the driver 34 to pass the dark state drive signal to the shutter assembly 14. When the sensor output signal indicates to the weld detect circuit 18 that the intense light is no longer present, the weld detect circuit 18 outputs a signal to the dark/light control 32 to cause the dark/light control 32 to switch the driver 34 to pass the clear state drive signal to the shutter assembly 14. As will be discussed in more detail below, the microcontroller 20 maintains the dark/light control 32 in the dark state for a predetermined delay period after the weld detect circuit 18 outputs the signal to the dark/light control 32.

The microcontroller 20 receives user input from the user interface 22. The user interface 22 can be any device capable of receiving user input, such as a keypad, microphone or the like. In a preferred embodiment shown in FIG. 1, the user interface 22 is provided with a keypad having a mode button 90 and an up/down button 94. The mode button 90 permits selection of predetermined modes of operation, such as a sensitivity adjustment, a delay adjustment, a shade adjustment and a "3n1" adjustment. The up/down button 94 permits adjustment of selections in each of the modes. The mode button 90 can be implemented as a switch, or a knob, for example. The up/down button 94 can be implemented as a switch, a knob, two different buttons, an encoder or a toggle switch, for example.

The display 24 shows various information relating to the modes and selections in each of the modes.

The sensitivity adjustment permits manual selection of the sensitivity of the sensor circuit 16. More particularly, the sensitivity of the sensor circuit 16 can be regulated by the microcontroller 20 by varying the predetermined threshold of the comparators 70, as indicated by a signal path 96.

The delay adjustment delays the passage of the clear state drive signal through the driver 34 for a selected time, thus preventing the shutter assembly 14 from switching to a clear state during brief "off" periods in the weld pulsations that exist with various weld types. Further, once the welding arc is extinguished, the work piece which is being welded may glow brightly for several milliseconds thereafter. The delay adjustment delays the clear state drive signal for the selected time so as to protect the individual's eyes from the glow of the work piece. The selected time is desirably between about 0.1 seconds to about 1 seconds. The selected time period for the delay can be set by a user utilizing the user interface 22. The microcontroller 20 delays the passage of the clear state drive signal by controlling the dark/light control 32 and thereby delaying the passage of the clear state drive signal to the shutter assembly 14.

The shade adjustment permits adjustment of the opacity of the shutter assembly 14 in the dark state. The shade adjustment is implemented by the microcontroller 20 controlling the shade control 30. In one preferred embodiment, the shade control 30 is a digital potentiometer, which functions as a voltage divider to control the voltage of the variable high voltage regulator 36.

The "3n1" adjustment permits selection of one of a plurality of modes referred to herein as a "torch mode", a "grind mode" and a "weld mode".

In the "torch mode" the microprocessor outputs a signal to the dark/light control 32 to maintain the shutter assembly 14 in the dark state regardless of the sensor output signal. In addition, in the "torch mode" the microprocessor outputs a signal to the shade control 30 to set the shade of the shutter assembly 14 to an opacity of about 5, 6, 7 or 8 so that the individual can see through the shutter assembly 14 when using a torch while still providing an adequate level of protection for the individual. The level of the shade control 30 in the torch mode can be predetermined and unchangeable by the user, or could be manually set by the user. For example, the level of the shade control 30 in the torch mode could be predetermined as a 5 or a 6. In this case, the user could not vary the level of the shade control 30. Alternatively, the microcontroller 20 could be programmed to permit the user to manually set the level of the shade control 30 in the torch mode.

In the "grind mode", the microcontroller 20 outputs a signal to the dark/light control 32 to maintain the shutter assembly 14 in the clear state regardless of the sensor output signal. In other words, in the grind mode, intense light caused by sparks, for example, will not switch the shutter assembly 14 to the dark state because the microcontroller 20 maintains the shutter assembly 14 in the clear state.

In the "weld mode", the weld detect circuit 18 controls the dark/light control 32 as discussed above so as to immediately switch the shutter assembly 14 to the dark state when an intense light is sensed without the aid or help of the microcontroller 20.

As discussed above, the microcontroller 20 can learn, and store information so as to provide other modes such as automatic light sensitivity, automatic shade control, memory presets, and selectable torch shade settings. These other modes can be selected via the mode button 90 or other input devices such as an external key. In the automatic light sensitivity mode, the microcontroller 20 continuously averages the light levels sensed by the sensor circuit 16. The light sensitivity can be implemented in at least two manners. In the first manner, when the microcontroller 20 senses a jump in the light wheels, then the microcontroller 20 outputs a signal to the dark/light control 32 to cause the shutter assembly 14 to switch to the dark state, and a signal to the HV control 40 to cause the HV pulse to be generated, as discussed above. In the second manner, the microcontroller 20 continuously averages the light levels sensed by the sensor circuit 16, and automatically varies the bias level of the comparators 70 to change the sensitivity of the weld detect circuit 18.

In the automatic shade control mode, the microcontroller 20 continuously monitors the intensity of the light once the shutter assembly 14 is switched to the dark state. The microcontroller 20 then controls the shade control 30 and varies the opacity of the shutter assembly 14 as the sensed light levels change so as to maintain a substantially constant amount of light passing through the shutter assembly 14.

The microcontroller 20 can also be programmed to provide for a plurality of memory presets with each memory preset having at least one predetermined setting. For example, if two users were going to use the same eye protection device 10, each user could have their own memory preset so that such users could select their memory preset before using the eye protection device 10. In this case, the memory presets would reduce the amount of time spent on manually changing the settings. Alternatively or in addition, the microcontroller 20 could store a plurality of memory presets for one user. For example, the user could have one memory preset for TIG welding, and another memory preset for MIG welding.

The microcontroller 20 can also be programmed to monitor and store various parameters relating to historical use of the eye protection device 10. For example, the parameters could be 1) unit on time, 2) unit dark time, and 3) average dark time. The stored parameters could be downloaded or viewed as an aid for monitoring working habits of the user, warranty returns, or troubleshooting.

The eye protection device 10 can also be provided with a communication device (not shown) for communicating with a computer, such as a personal computer, mini computer, mainframe computer, palm computer or personal data assistant. The communication device can be a wireless communication device, such as an optical link, or another type of communication device, such as a modem. The communication device can be used for downloading various parameters or data stored in the eye protection device 10 to the computer so that such parameters or data can be reviewed or used for other applications. Or, the communication device could be used to upload new programming, or settings to the eye protection device 10. The new programming or settings could be used to upgrade the eye protection device 10 to provide new modes or functions. Alternatively, the new programming or settings could be used to provide new settings based on such factors as type of lighting. Further, the microcontroller 20 can be programmed to provide a self-test mode, and to display an indication of expected battery life on the display 24. In the self-test mode, the microcontroller 20 would run tests on various components of the eye protection device 10, such as the display 24, the power supply 26 or the shutter a assembly 14. If any of the components are not working properly, an error code can be displayed by the display 24. The expected battery life can be determined by monitoring the length of time that a battery has been installed ("actual length of time") in the eye protection device 10. By subtracting the actual length of time from a predetermined expected battery life, an estimated remaining battery life can be determined. The estimated remaining battery life is then displayed on the display 24 so as to communicate the estimated remaining battery life to the user. The estimated remaining battery life can also be determined by placing a predetermined load on the battery and then monitoring the decrease of the battery voltage during the load time. This is a well known method for measuring battery life. Thus, no further comments are deemed necessary to teach one skilled in the art how to use this method to estimate the remaining battery life.

To conserve energy, the microcontroller 20 is programmed with a sleep mode so as to reduce the amount of energy utilized when the microcontroller 20 is not in use. The microcontroller 20 continuously runs the programming for the sleep mode. In general, the microcontroller 20 is programmed to go to sleep when idle and wake up upon detection of certain predetermined events. The predetermined events can be 1) the detection of a weld, as discussed above, 2) the polarity of the dark state drive signal or the clear state drive signal needing to be switched, 3) the display 24 needing to be updated, and 4) the reception of a signal from the user interface 22.

As discussed above, the polarity of the dark state drive signal or the a clear state drive signal is switched about 70 to about 120 times per second. Thus, the sleep mode causes the microcontroller 20 to "wake up" at least about 70 to about 120 times per second (depending on the frequency of oscillation for the clear state and dark state drive signals), i.e., when needed to output a signal to the driver 34 and thereby switch the polarity of the dark state drive signal or the clear state drive signal.

Figure 14:
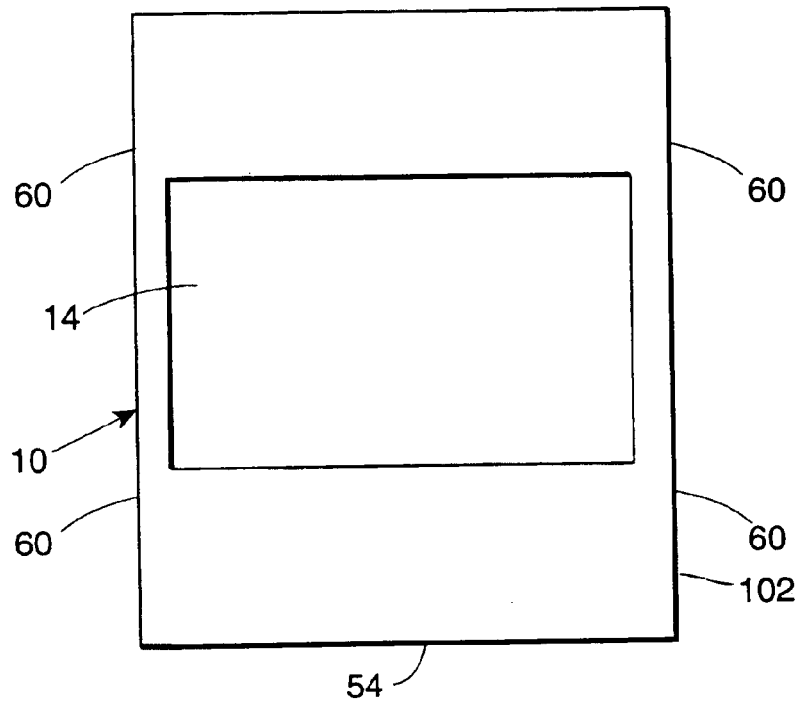
FIG. 14 is front perspective view of the eye protection device.
Figure 15:
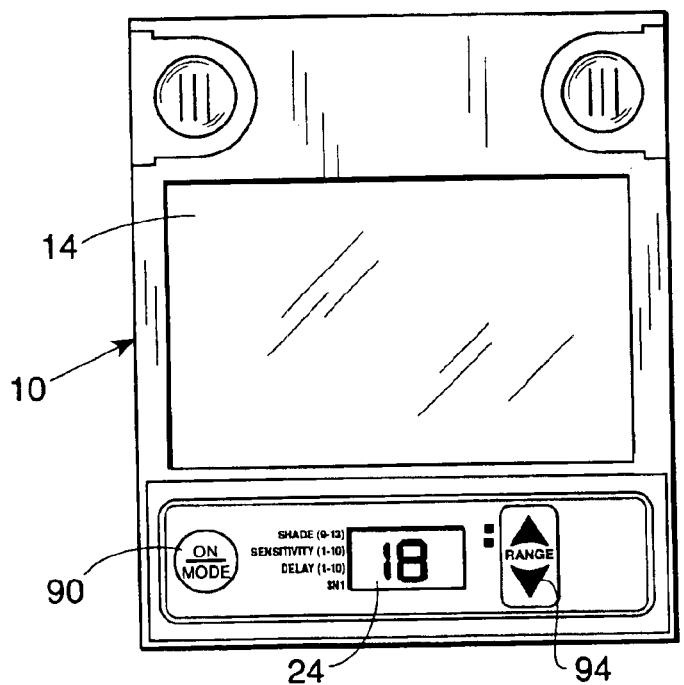
FIG. 15 is a rear perspective view of the eye protection device.

Although in the preferred embodiment depicted in FIGS. 14 and 15, the control circuit 12 and the shutter assembly 14 are positioned in a same housing 102, it should be understood that the control circuit 12 and the shutter assembly 14 could also be positioned in different housings. For example, the control circuit 12 could be supported on the user's belt, while the shutter assembly 14 could be supported by the welding helmet. A cable could extend from the control circuit 12 to the shutter assembly 14 to transmit the dark state drive signal and the clear state drive signal to the shutter assembly 14. Further, the input or controls for the control circuit 12 could be supported on the outside of the user's welding mask or helmet.

Figure 2A:
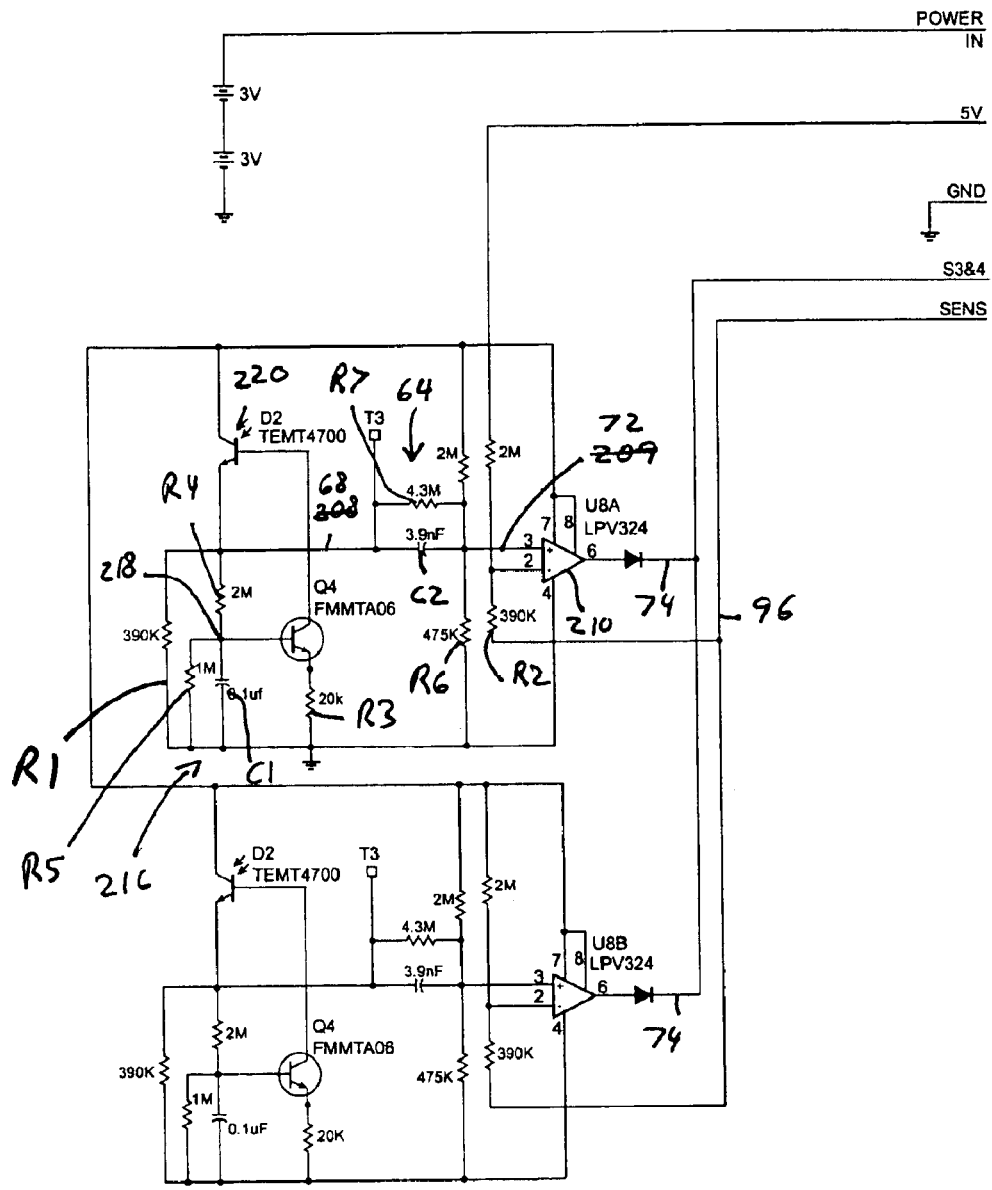
FIGS. 2A–2C are a schematic diagram of a control circuit of the eye protection device depicted in FIG. 1.
Figure 2B:
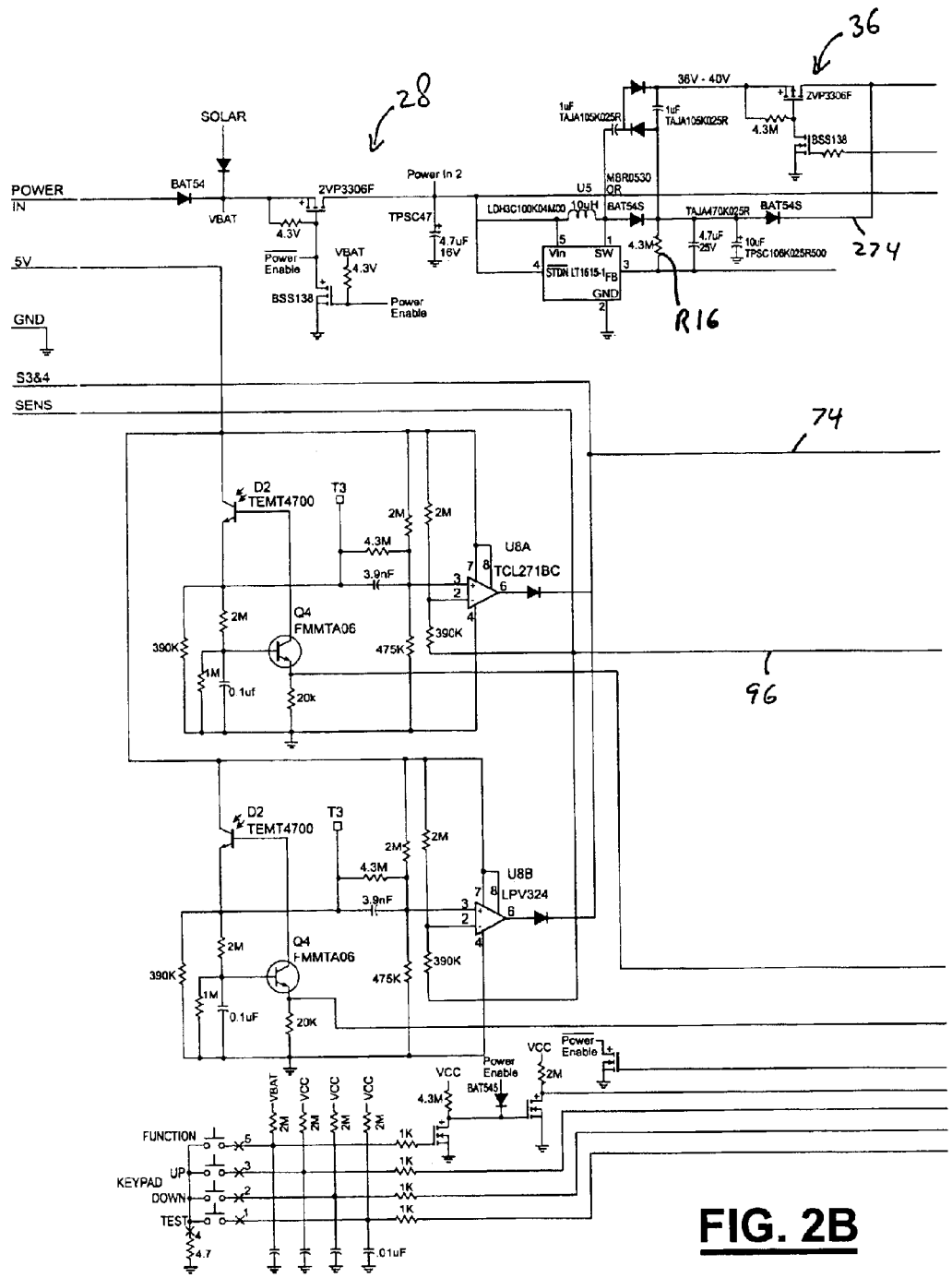
Figure 2C:
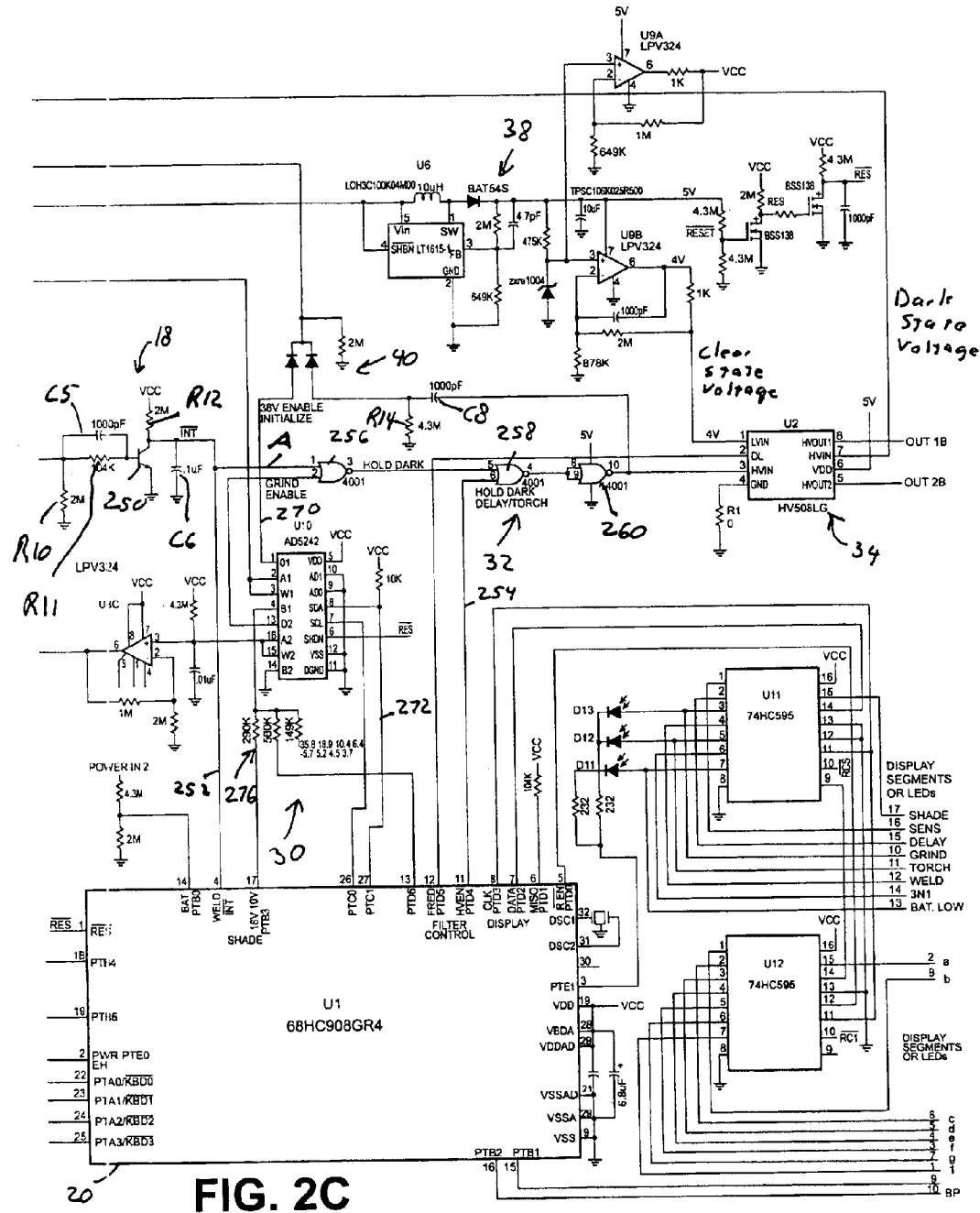

Shown in FIG. 2A-2C is one embodiment of the control circuit 12. The control circuit 12 will now be described in more detail.

The sensor circuit 16 includes the plurality of sensors 60 for detecting the presence of light and outputting a sensor output signal representative of the level of light detected. The sensors 60 include one or more phototransistor D2 with the output of the phototransistor D2 coupled to feedback circuits 206. The output of phototransistor D10 is sent to line 68. A load resistor R1 is connected between line 68 and ground. The signal filter 64 couples line 68 to line 72. Line 72 is connected to the noninverting input of amplifier 210. Amplifier 210 is preferably configured as closed loop noninverting amplifier. The gain, and thus the sensitivity of the amplifier 210 is controlled via the line 96 and the feedback resistor R2. The output of amplifier 210 on line 74 serves as the sensor circuit output. Line 74 is connected to the input of the weld detect circuit 28.

The feedback circuit 206 for the phototransistor D2 comprises a resistor capacitor circuit 216 connected between the emitter of the phototransistor D2 and ground, and a feedback transistor Q4 having a base coupled to line 218 of the resistor capacitor circuit 216, a collector coupled to the base of the phototransistor D2, and an emitter coupled to the ground via resistor R3.

Phototransistor D2 serves as the weld sensor. It receives an input of incident light 220 and produces an output on line 68 representative of the intensity of the incident light. The phototransistor D2 used in the present invention is preferably a planar phototransistor configured for a surface mount. The planar phototransistor is smaller than conventional metal can phototransistors, thus allowing a reduction in size of the unit in which the sensor circuit is implemented. While the metal can phototransistors used in the sensor circuits of the prior art had a thickness of about ½ inch, the planar phototransistors with a surface mount used in the present invention have a thickness of only about ¼ inch. This reduction is thickness allows the sensor circuit to be implemented into a smaller and sleeker unit. Further, the surface mount configuration of the phototransistor D2 allows the phototransistor to be easily affixed to a circuit board. The inventor herein has found that the TEMT4700 silicon npn phototransistor manufactured by Vishay-Telefunken is an excellent phototransistor for the present invention as it has a smaller size than conventional metal can phototransistors and allows the sensor circuit to maintain a constant signal level without excessive loading or the drawing of excessive current.

The resistor capacitor circuit 216 and the feedback transistor Q4 in the phototransistor feedback circuit 206 function to adjust the sensitivity of the phototransistor D2. The resistors R4 and R5 and capacitor C1 are chosen to be of a size to provide a relatively large time constant, and therefore a relatively slow response to changes in voltage on line 68. The delay exists because of the time it takes for the voltage on line 218 to charge to an amount sufficiently large to activate Q4. Exemplary values for R5 and R4 are 1 MΩ and 2 MΩ respectively. An exemplary value for C1 is 0.1 $\mu$F. A detailed description of the operation of the resistor capacitor circuit 216 and feedback transistor Q4 can be found in prior patents 5,248,880 and 5,252,817, the disclosures of which have been incorporated by reference.

The signal on line 68 is fed into the amplifier 210. The signal is first passed through the high pass circuit (signal filter 64) formed by capacitor C2 to block the DC component of the detected signal. Line 72 contains the DC blocked detected signal. The current on line 72 is diverted to ground via resistor R6.

The sensor circuit 16 operates in the presence of both AC welds and DC welds. In an AC weld (also known as a MIG weld), the welding light is pulsating. Thus, the phototransistor D2 will detect a pulsating light signal. The frequency of the pulsations is often 120 Hz. In a DC weld (also known as a TIG weld), the welding light is substantially continuous, with the exception of a small AC component. When an AC weld is present, the phototransistor D2 will produce a pulsating output on line 68. The variations in the voltage signal due to the pulses will be passed through the capacitor C2 to line 72 and fed into the amplifier 210. The amplifier 210 will then provide gain for the signal on line 74 which is sufficient to trigger the delivery of the "dark state" drive signal to the shutter assembly 14.

When a DC weld is present, the phototransistor D2 will quickly produce an output on line 68 catching the rising edge of the DC weld. This sudden rise in voltage on line 68 will be passed through to the amplifier 210 causing a signal on line 74 sufficient to trigger the delivery of a "dark state" drive signal to the shutter assembly 14. Thereafter, capacitor C2 will block the DC component of the DC weld, allowing only the AC variations in the DC weld to pass through to the amplifier 210. A non-reactive element, e.g., resistor R7, is positioned in parallel with the high-pass filter circuit formed by the capacitor C2. The non-reactive element provides a DC bias to the input of the amplifier 210 to aid in the detection of the DC weld. That is, the brighter the light being generated from the weld becomes, the more sensitive the sensor circuit 16 becomes. In one embodiment, R7 can have a value of 4.3 M ohm. The amplifier 210 can be a closed loop, noninverting amplifier.

As discussed above, the outputs of the comparators 70 are Ored together so that if any one of the comparators 70 detects a weld, the weld detect circuit 18 will be activated. The weld detect circuit 18 includes an electronic switch 250, resistors R10, R11 and R12, and capacitors C5 and C6. When a weld is detected, the electronic switch 250 is activated through the resistor R11. The capacitor C5 connected to the base of the electronic switch 250 discharges when the weld is detected and thereby enhances the switching speed of the electronic switch 250.

When the electronic switch 250 switches, the capacitor C6 discharges thereby causing a logical "low" to be transmitted. The capacitor C6 and the resistor R12 form an RC circuit having a time constant which causes the capacitor C6 to charge at a predetermined rate. The signals received by the electronic switch 250 are typically in the form of short spikes caused by the sputtering of the weld. The time constant of the RC circuit should be tuned so that the output of the electronic switch 250 remains low between the spikes. The time constant can vary widely, however, a suitable time constant has been found to be between 1 and 100 milliseconds.

In response to the output of the electronic switch 250 going low, a signal is transmitted to the microcontroller 20 via a line 252, and to the dark/light control 32 via a line A. The signal received by the microcontroller 20 interrupts the microcontroller 20 to wake up the microcontroller 20. The microcontroller 20 then outputs a signal to the dark/light control 32 via a line 254. Thus, either the weld detect circuit 18 or the microcontroller 20 can cause the dark/light control 32 to switch the shutter assembly to the dark state.

In particular, the low signal is output by the weld detect circuit 18 to one input of a nor gate 256. In the weld mode, the other input of the nor gate 256 is held high. Thus, when the low signal is received by the nor gate 256, the output of the nor gate 256 goes high. The output of the nor gate 256 is fed to an input of a nor gate 258. The nor gate 258 has at least two inputs. One of the inputs is connected to the microcontroller 20 and the other input receives the output of the nor gate 256 as discussed above. The input of the nor gate 258 connected to the microcontroller 20 can be characterized as a hold dark, delay/torch line in that a high signal on such input will maintain the output of the nor gate 258 low, which in effect maintains the shutter assembly in the dark state.

The high signal provided to the nor gate 258 by the nor gate 256 causes the output of the nor gate 258 to go low. The low signal is provided to an inverter (formed by a nor gate 260 having both inputs tied together) which provides a high signal to a "high voltage in line" of the driver 34. This causes the driver 34 to pass the dark state drive signal to the shutter assembly, rather than the clear state drive signal.

The output of the nor gate 260 is also provided to a capacitor C8 of the HV control 40. As discussed above, the HV control 40 communicates with the variable high voltage regulator 36 so as to control the switching of the first and second signals to form the HV pulse followed by the constant voltage. The HV control 40 can be formed by an RC circuit (shown as resistor R14 and capacitor C8) with the time constant of the RC circuit determining the time period of the HV pulse. The microcontroller 20 communicates with the HV control 40 via lines 270 and 272) when the eye protection device 10 is turned on so as to initialize the shutter assembly 14.

During initialization, the shutter assembly 14 is enabled to the dark state for a predetermined time period. In the preferred embodiment depicted in FIG. 2, the microcontroller 20 only communicates with the HV control 40 to initialize the shutter assembly 14.

The shade control 30 adjusts the voltage level of the second signal (shown as the line 274) so as to adjust the opacity of the shutter assembly 14 in the dark state. For example, the shade control 30 can be formed by a digital potentiometer 276 positioned in a voltage divider circuit formed with a resistor R16.

Figure 3:
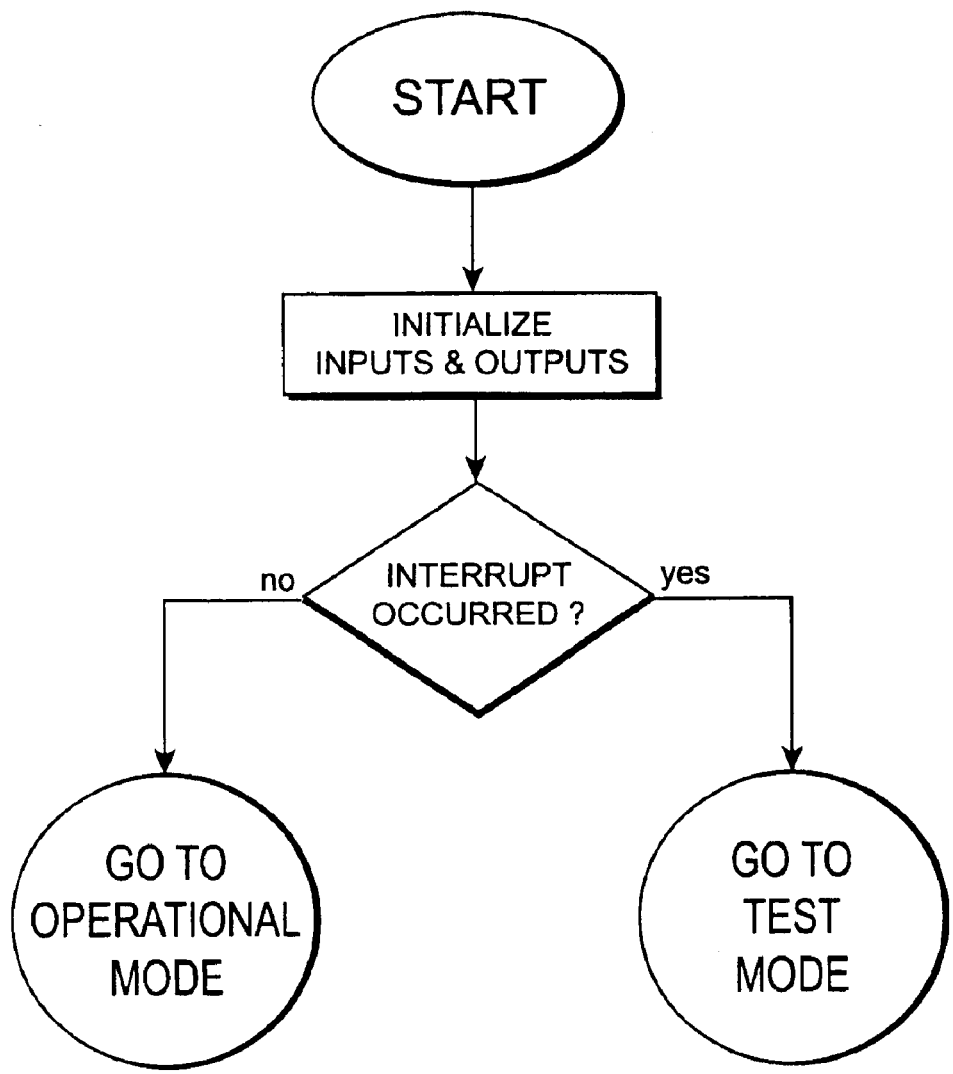
FIGS. 3–13 are flow diagrams illustrating the logic flow of one preferred embodiment of the present invention.
Figure 4:
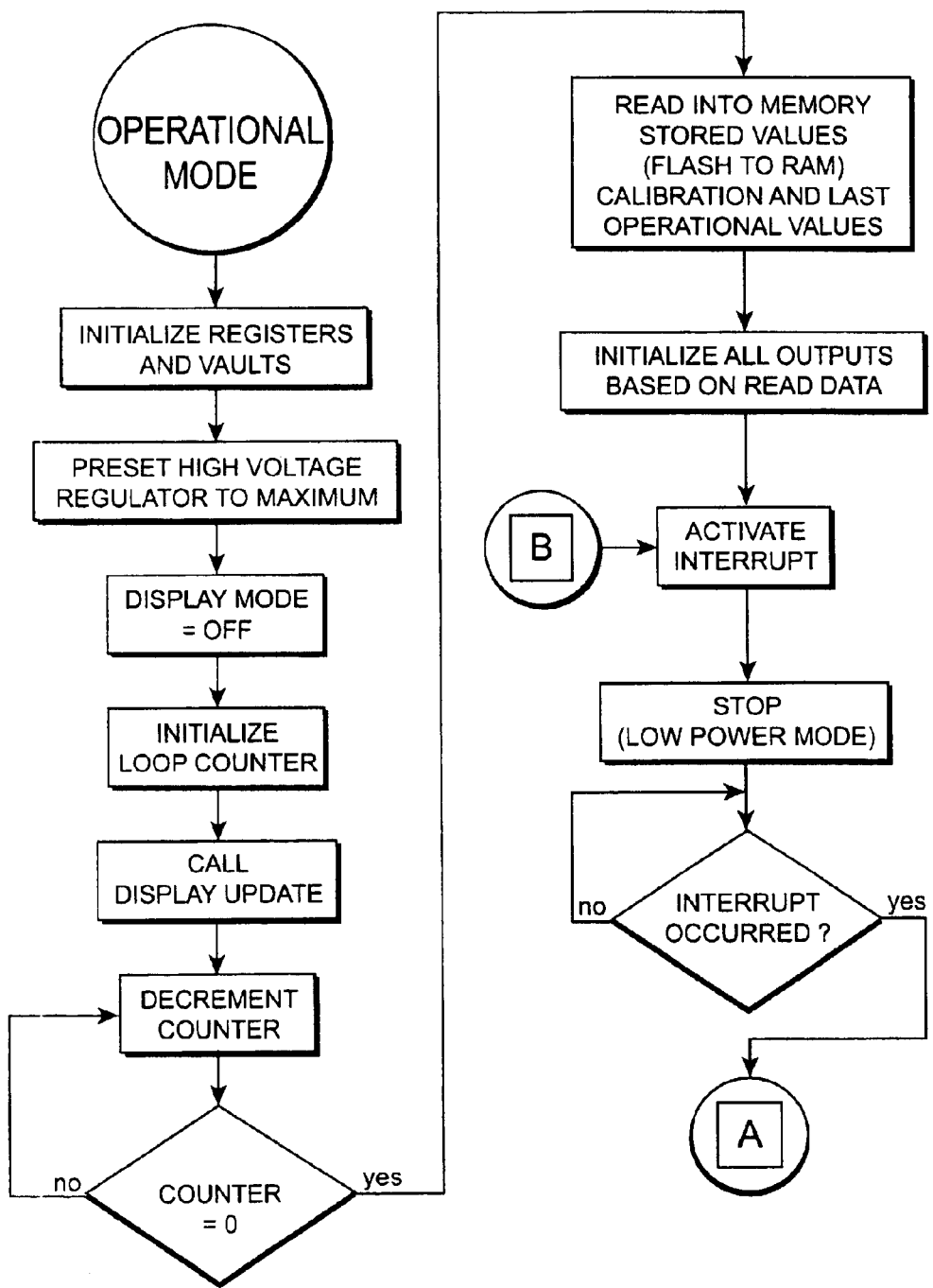
Figure 5:
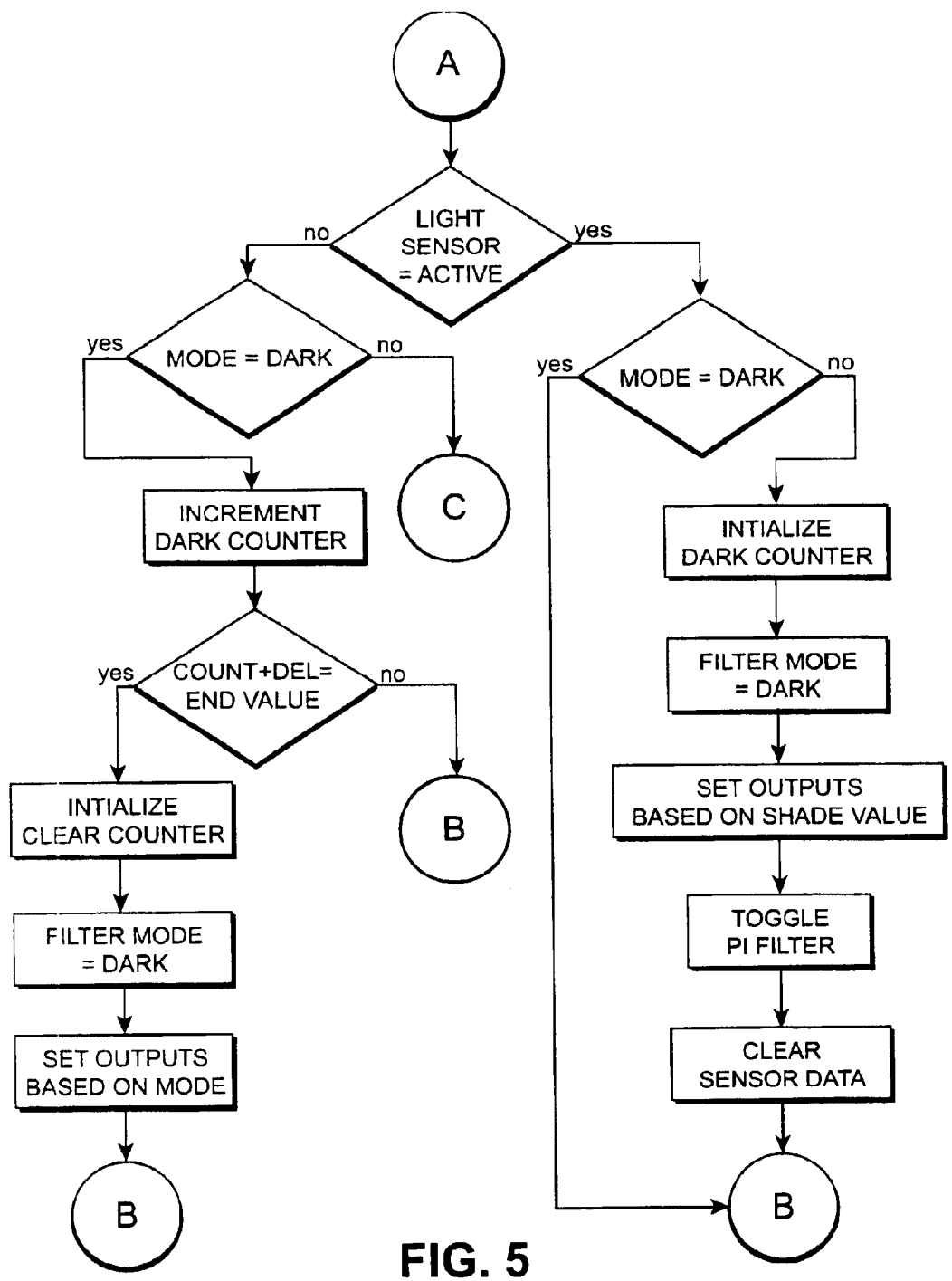
Figure 6:
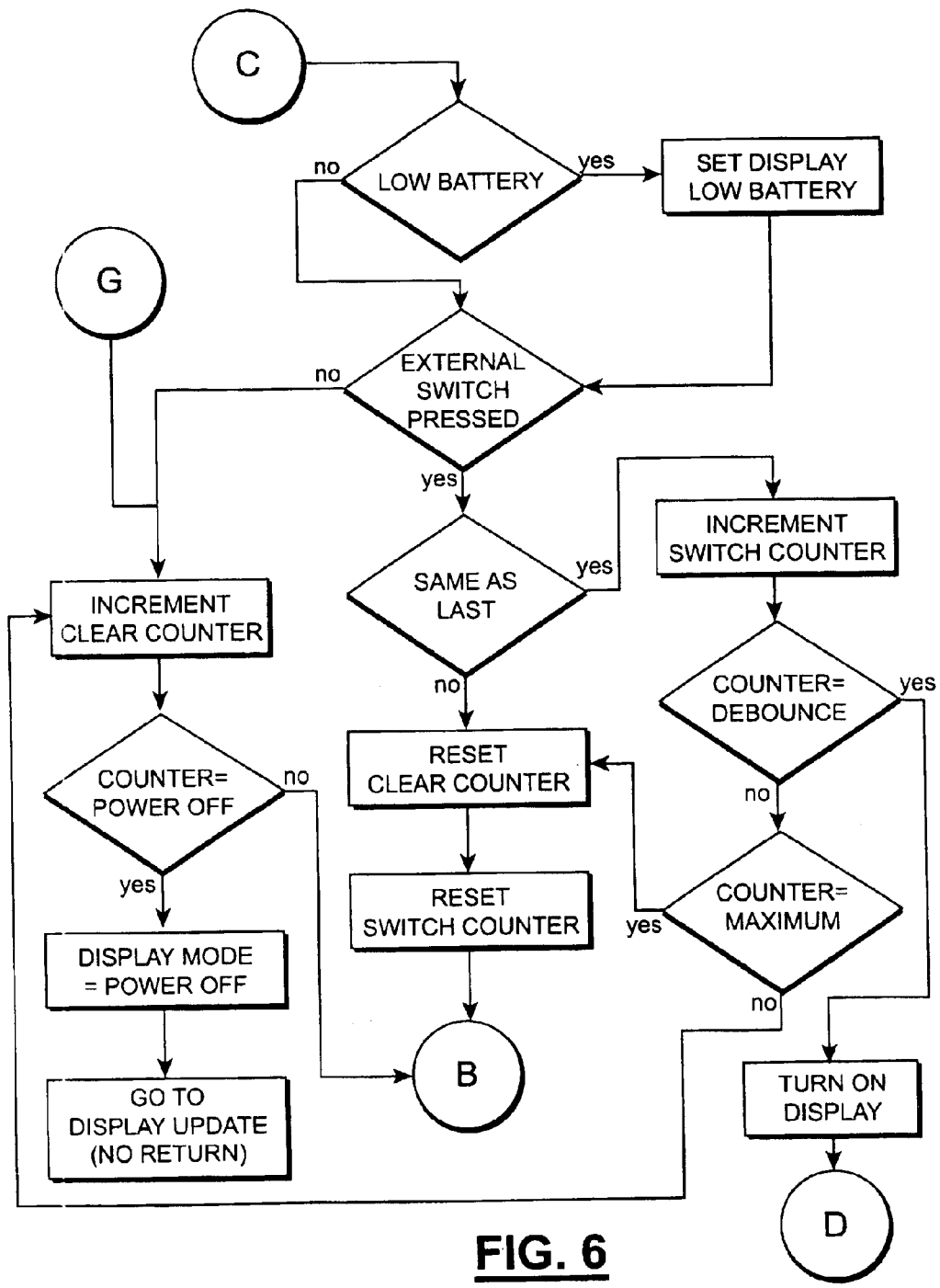
Figure 7:
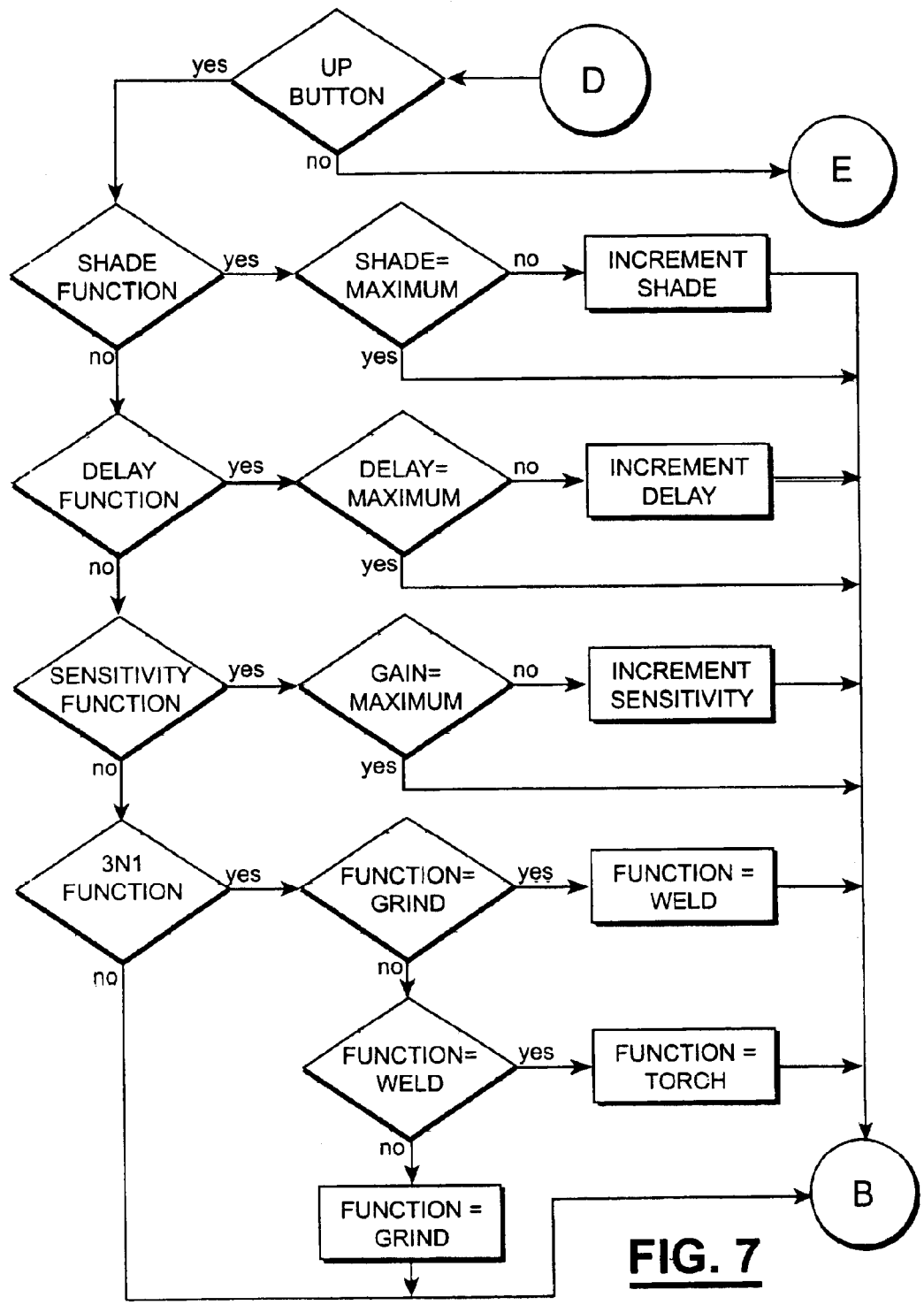
Figure 8:
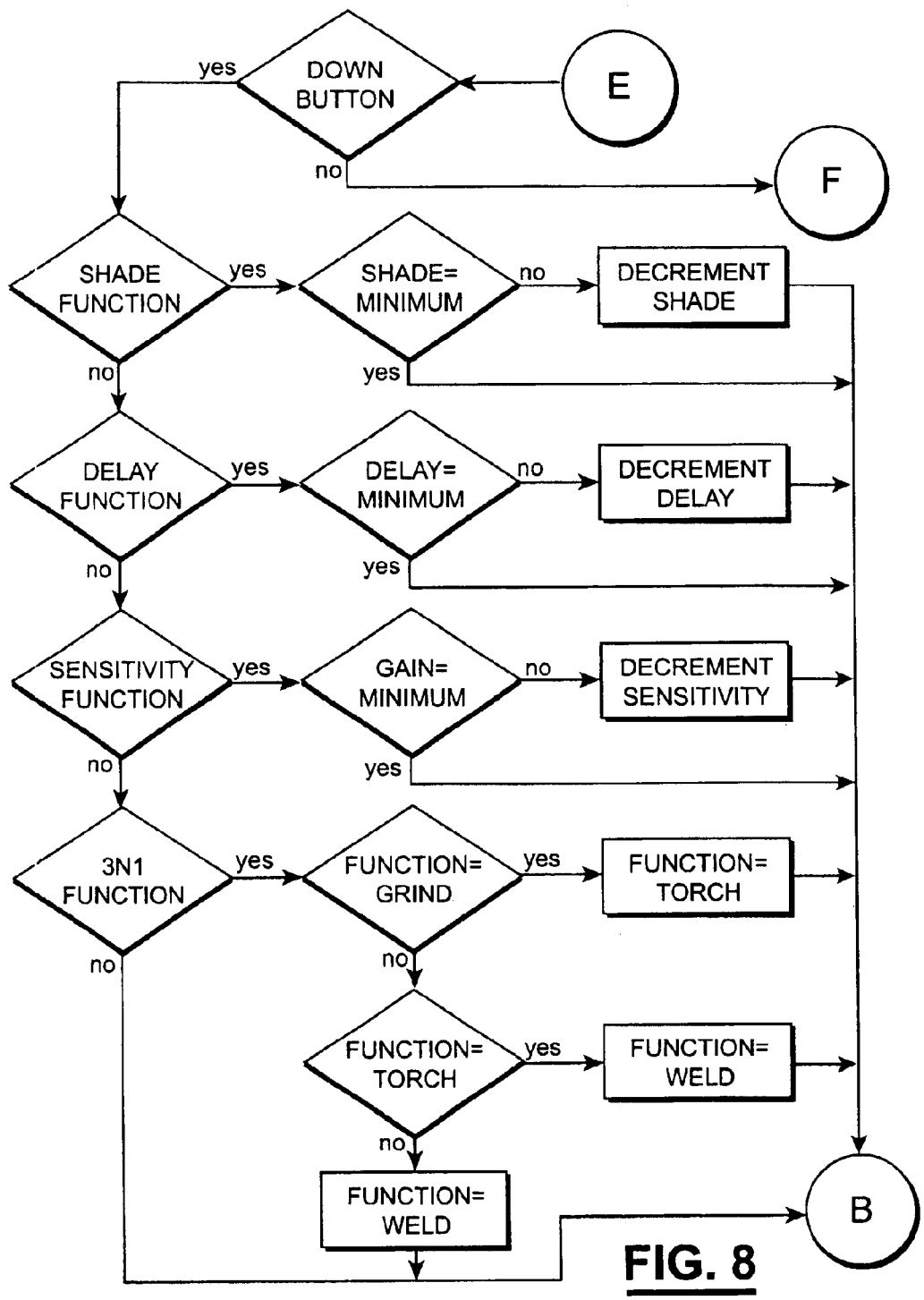
Figure 9:
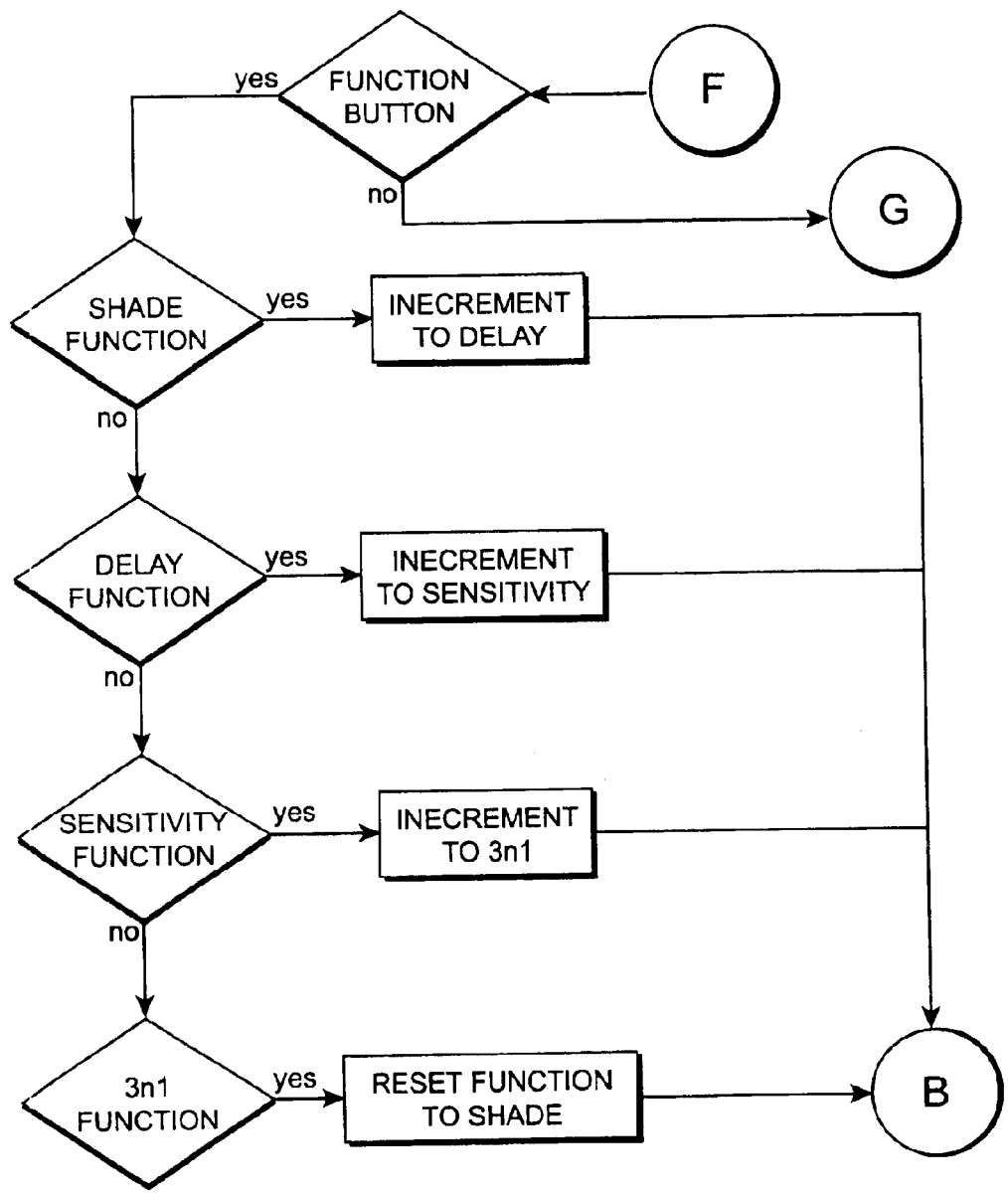
Figure 10:
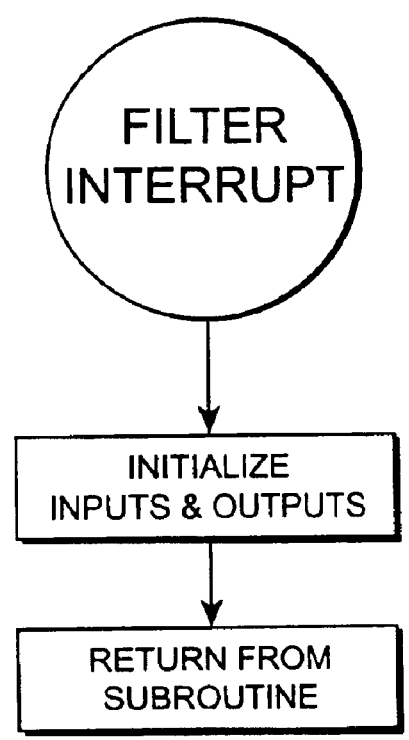
Figure 11:
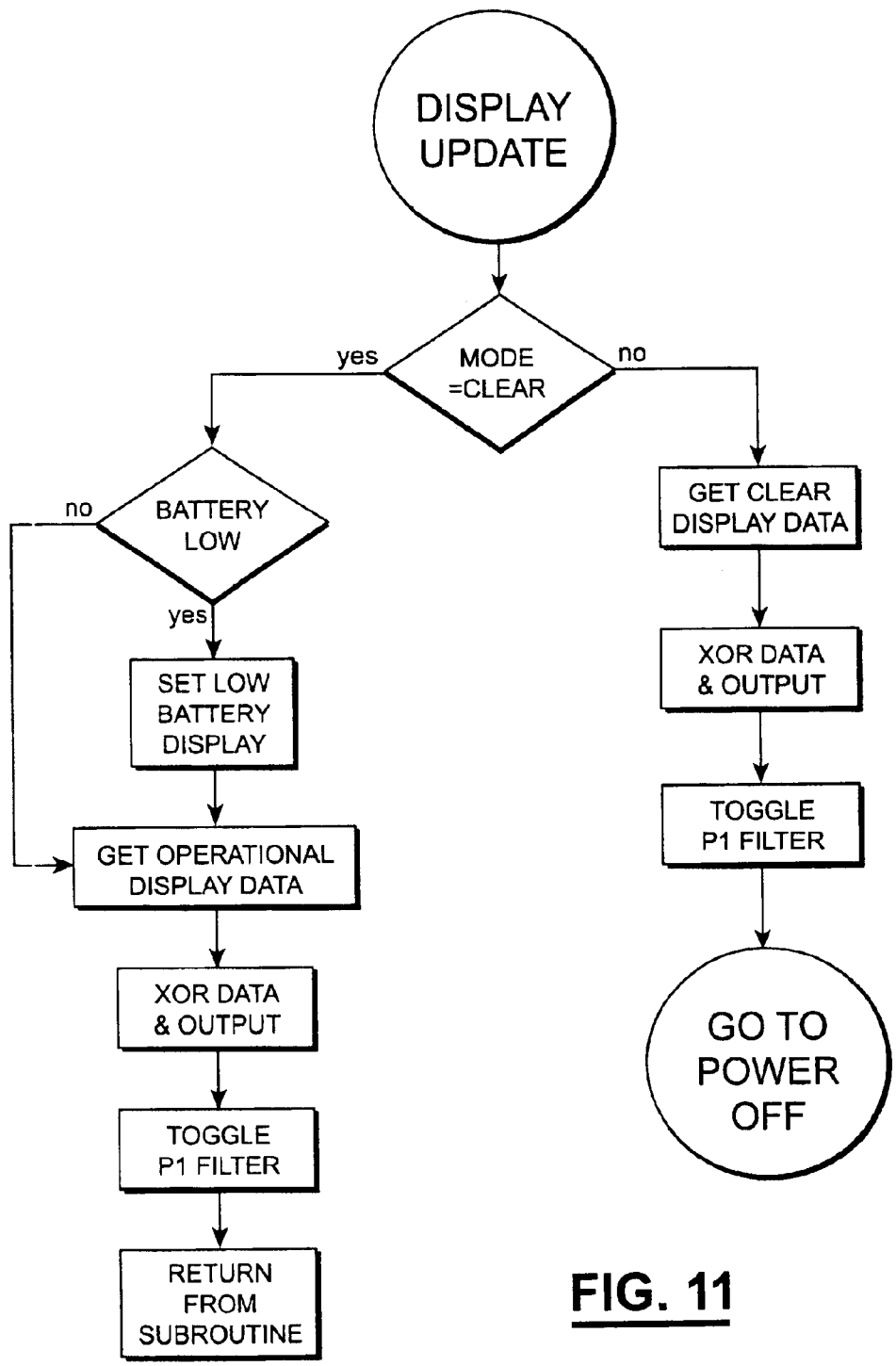
Figure 12:
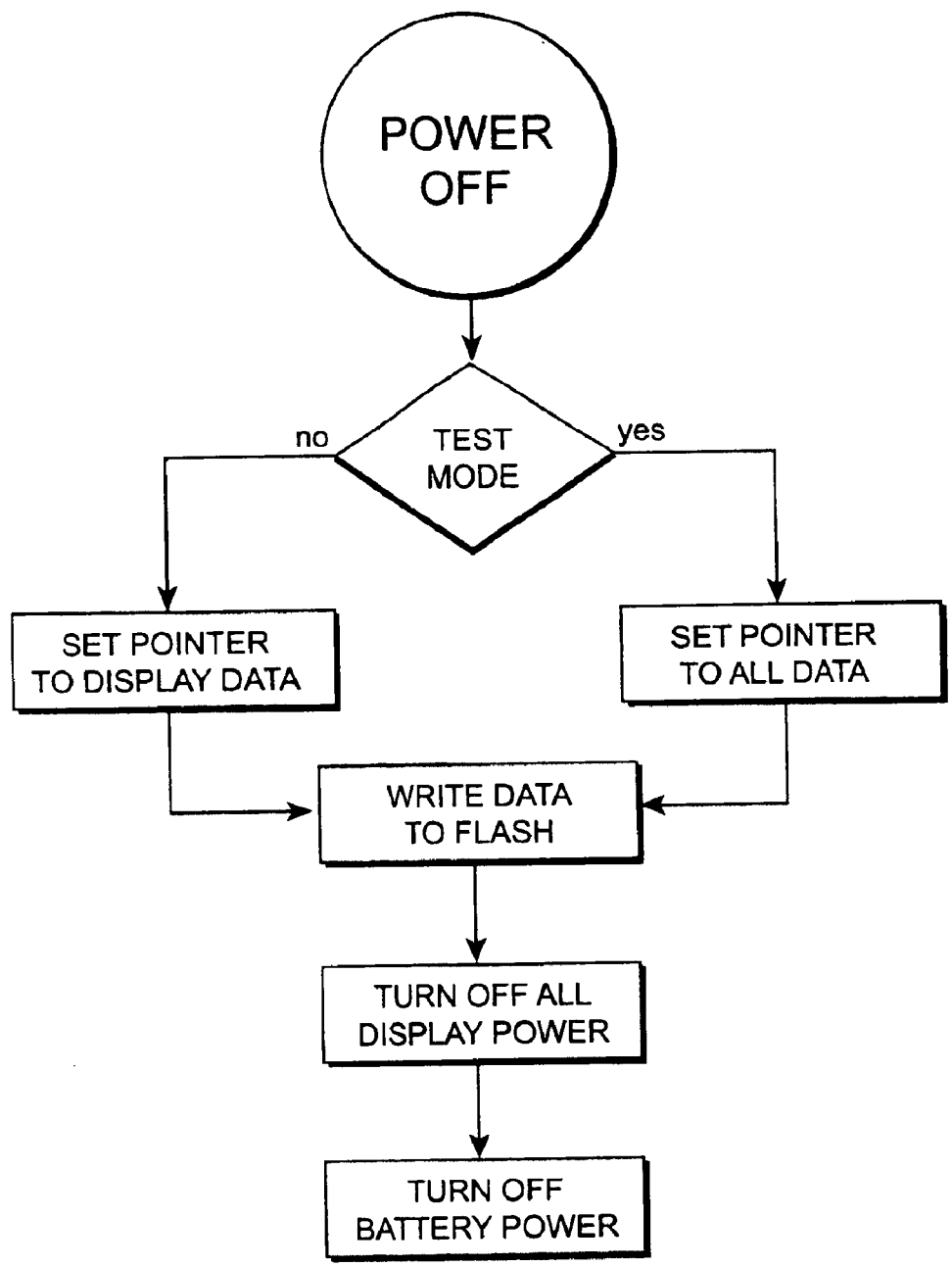
Figure 13:
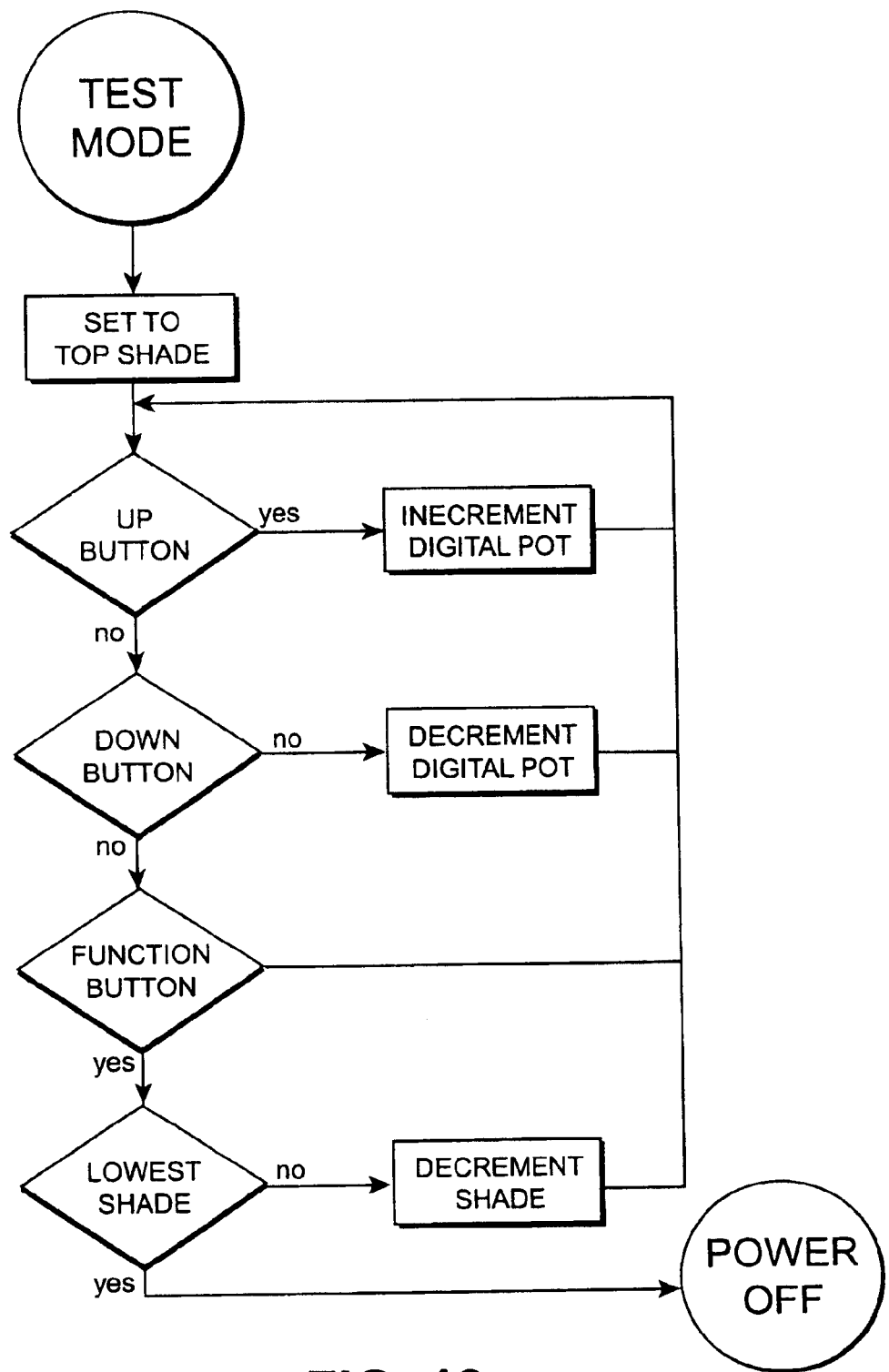

The logic flow of the microcontroller 20 of the eye protection device 10 is shown in FIGS. 3–13. FIG. 3 shows a startup routine for initialization of the ports and determining whether to branch into an operational mode or a test mode. FIG. 4 shows the logic for the operational mode of the microcontroller 20. FIG. 5 shows the logic for a decision making routine following the receipt of an interrupt. FIG. 6 shows the logic flow when an interrupt occurred and such interrupt was not caused by the sensor circuit. FIGS. 7, and 9 show the logic flow to determine whether the up button, down button or function button was pressed and the action needed to be performed. FIG. 10 shows the logic flow for a timer routine for toggling the shutter assembly 14 and the display at a periodic rate. FIG. 11 shows the logic flow for updating information to the display. FIG. 12 shows the logic flow of a power off routine. FIG. 13 shows the logic flow for the test mode for calibrating the initial shade values.

Changes may be made in the embodiments of the invention decribed herein, or in the parts or the elements of the embodiments described herein, or in the steps or sequence of steps of the methods described herein, without departing from the spirit and/or the scope of the invention as defined in the following claims.

What is claimed is:

1. An auto darkening eye protection device comprising:
    a shutter assembly adjustable between a clear state and a dark state; and
    a control circuit comprising:
        a microcontroller;
        a delivery circuit simultaneously receiving a dark state signal and a clear state signal and outputting a dark state drive signal to the shutter assembly to switch the shutter assembly from the clear state to the dark state upon enablement of the delivery circuit;
        a sensing circuit for sensing the occurrence of a welding arc and providing an output indicative of the occurrence of the welding arc;
        a weld detect circuit receiving the output of the sensing circuit, the weld detect circuit enabling a dark state drive signal to be delivered to the shutter assembly by the delivery circuit; and a dark/light control receiving input from at least one of the weld detect circuit and the microcontroller and outputting signals to the delivery circuit in response thereto, the signals provided to the delivery circuit controlling passage of the dark state signal and the clear state signal to the shutter assembly.

2. An auto darkening eye protection device comprising:

a shutter assembly adjustable between a clear state and a dark state; and a control circuit comprising:
　a microcontroller;
　a delivery circuit outputting a dark state drive signal to the shutter assembly to switch the shutter assembly from the clear state to the dark state upon enablement of the delivery circuit;
　a sensing circuit for sensing the occurrence of a welding arc and providing an output indicative of the occurrence of the welding arc;
　a weld detect circuit receiving the output of the sensing circuit, the weld detect circuit enabling a dark state drive signal to be delivered to the shutter assembly by the delivery circuit;
　a variable high voltage regulator continuously generating a first and second signal having different voltages and forming the dark state drive signal; and
　wherein the dark state drive signal includes a high voltage pulse followed by a constant voltage, the high voltage pulse having a voltage in a range from about 30 V to about 120 V, and a time period in a range from about 10 microseconds to about 100 milliseconds, the first signal being passed to the delivery circuit for a selected time period to form the high voltage pulse, at the end of which the second signal is passed to the delivery circuit to form the constant voltage.

3. The auto darkening eye protection device of claim 2, further comprising a HV control communicating with the variable high voltage regulator so as to control the switching of the first and second signals to form the high voltage pulse followed by the constant voltage, the HV control being formed by at least one of an RC circuit having a time constant determining the time period of the high voltage pulse, or a microcontroller controlling the HV control.

4. The auto darkening eye protection device of claim 3, wherein the microcontroller communicates with the HV control upon initialization of the control circuit so as to enable the shutter assembly to the dark state for a predetermined time period.

5. The auto darkening eye protection device of claim 4, wherein the microcontroller only communicates with the HV control to initialize the shutter assembly.

6. An auto darkening eye protection device comprising:

a shutter assembly adjustable between a clear state and a dark state; and a control circuit comprising:
　a microcontroller, wherein the microcontroller includes an automatic light sensitivity mode;
　a delivery circuit outputting a dark state drive signal to the shutter assembly to switch the shutter assembly from the clear state to the dark state upon enablement of the delivery circuit;
　a sensing circuit for sensing the occurrence of a welding arc and providing an output indicative of the occurrence of the welding arc;
　a weld detect circuit receiving the output of the sensing circuit, the weld detect circuit enabling a dark state drive signal to be delivered to the shutter assembly by the delivery circuit; and
　wherein in the automatic light sensitivity mode, the microcontroller automatically varies the sensitivity of the weld detect circuit.

7. The auto darkening eye protection device of claim 6, wherein the sensor circuit comprises:

a light sensor having a light sensor output;

a comparator having an input coupled to the light sensor for triggering the weld detect circuit to enable the dark state drive signal when the light sensor receives a light input above a bias level thereby indicating the presence of a welding arc; and wherein the microcontroller varies the bias level of the comparator to vary the sensitivity of the weld detect circuit.

* * * * *

UNITED STATES PATENT AND TRADEMARK OFFICE
CERTIFICATE OF CORRECTION

PATENT NO. : 6,881,939 B1 Page 1 of 1
APPLICATION NO. : 10/140049
DATED : April 19, 2005
INVENTOR(S) : Thomas J. Hamilton et al.

It is certified that error appears in the above-identified patent and that said Letters Patent is hereby corrected as shown below:

Column 2,
Line 9, delete first occurrence of "a".

Column 6,
Line 11, after "light" delete "wheels" and add -- levels --.

Column 7,
Line 2, after "shutter" delete "a".
Line 32, after "the" and before "clear" delete "a".

Column 10,
Line 47, after "tion" and before "herein" delete "decribed" and add -- described --.

Signed and Sealed this

Twenty-seventh Day of June, 2006

JON W. DUDAS
*Director of the United States Patent and Trademark Office*